US008740765B1

(12) United States Patent
Fischell et al.

(10) Patent No.: US 8,740,765 B1
(45) Date of Patent: Jun. 3, 2014

(54) MAGNETIC PULSING SYSTEM FOR INDUCING ELECTRIC CURRENTS IN A HUMAN BODY

(75) Inventors: Robert E. Fischell, Dayton, MD (US); Scott J. S. Fischell, Glenelg, MD (US); David R. Fischell, Fair Haven, NJ (US); Emily Ma, Mountain View, CA (US); Kuen Chang, Evanston, IL (US); Dave Vondle, Chicago, IL (US); Benjamin Pless, Atherton, CA (US)

(73) Assignee: Eneura, Inc., Sunnyvale, CA (US)

( * ) Notice: Subject to any disclaimer, the term of this patent is extended or adjusted under 35 U.S.C. 154(b) by 0 days.

(21) Appl. No.: 13/571,833

(22) Filed: Aug. 10, 2012

Related U.S. Application Data

(63) Continuation of application No. 11/305,276, filed on Dec. 19, 2005, now Pat. No. 8,262,556.

(51) Int. Cl.
*A61N 2/04* (2006.01)

(52) U.S. Cl.
USPC ............................................................ 600/14

(58) Field of Classification Search
USPC .................. 600/9–15; 601/15–22; 606/32–52
See application file for complete search history.

(56) References Cited

U.S. PATENT DOCUMENTS

| 4,464,608 | A |   | 8/1984  | Pilley |           |
|-----------|---|---|---------|--------|-----------|
| 4,480,596 | A |   | 11/1984 | Shumiyashu |       |
| 4,654,574 | A |   | 3/1987  | Thaler |           |
| 4,940,453 | A | * | 7/1990  | Cadwell ............................ | 600/13 |
| 5,105,156 | A | * | 4/1992  | Bohmer ............................ | 324/435 |
| 5,267,938 | A | * | 12/1993 | Konotchick ...................... | 600/9 |
| 5,338,286 | A |   | 8/1994  | Abbott et al. |       |
| 5,524,624 | A | * | 6/1996  | Tepper et al. ................... | 600/439 |
| 5,658,322 | A | * | 8/1997  | Fleming ........................... | 607/50 |
| 6,061,593 | A |   | 5/2000  | Fischell et al. |   |
| 6,770,022 | B2 |  | 8/2004  | Mechlenburg et al. |   |
| 7,294,101 | B2 |  | 11/2007 | Fischell et al. |   |
| 2002/0019587 | A1 | | 2/2002 | Cheng et al. |   |
| 2003/0130709 | A1 | * | 7/2003 | D.C. et al. ..................... | 607/88 |
| 2003/0144711 | A1 | * | 7/2003 | Pless et al. ..................... | 607/60 |
| 2004/0088024 | A1 | * | 5/2004 | Firlik et al. .................... | 607/45 |
| 2004/0122281 | A1 | * | 6/2004 | Fischell et al. ................ | 600/13 |
| 2005/0186953 | A1 | | 8/2005 | Harris |   |
| 2006/0047316 | A1 | | 3/2006 | Fischell et al. |   |

FOREIGN PATENT DOCUMENTS

| JP | 59-218165 A | 12/1984 |
| JP | 3-146073 A | 6/1991 |
| JP | 9-84886 A | 3/1997 |

(Continued)

*Primary Examiner* — Charles A Marmor, II
*Assistant Examiner* — Catherine B Kuhlman
(74) *Attorney, Agent, or Firm* — Rosenberg, Klein & Lee

(57) ABSTRACT

Disclosed is a means and method for the treatment of migraine headaches and other disorders of the human body by the application of one or more intense magnetic pulses. By placing an intense magnetic field pulse(s) onto a certain region of the brain, an electrical current can be generated in the cerebral cortex that can stop a migraine headache in some patients or at least decrease its severity. The device to perform this function can be called a "magnetic pulser system." This system can be made in one piece and powered by plugging into a household or automobile receptacle or from a battery. The pulser system uses capacitors that are first charged to a high voltage and then discharged into a coil that creates the intense magnetic pulse. Both visual and auditory signals can be provided by the pulser system to assist the patient in using the device.

13 Claims, 3 Drawing Sheets

(56) References Cited

FOREIGN PATENT DOCUMENTS

| JP | 2002-306614 A | 10/2002 |
| JP | 2004-511314 A | 4/2004 |
| JP | 2004-329584 A | 11/2004 |
| WO | 02/32504 A2 | 4/2002 |
| WO | 2005/065768 A1 | 7/2005 |
| WO | 2006/133564 A1 | 12/2006 |

* cited by examiner

MAGNETIC PULSING SYSTEM FOR INDUCING ELECTRIC CURRENTS IN A HUMAN BODY

RELATED APPLICATIONS

This patent application is a Continuation of patent application Ser. No. 11/305,276, filed on 19 Dec. 2005.

FIELD OF USE

This invention is in the field of methods and devices for the treatment of certain human disorders, particularly for the treatment of diseases of the brain.

BACKGROUND OF THE INVENTION

Migraine headaches occur in approximately 12% of the world population. Therefore, in the United States in the year 2005 there are approximately 30 million people who suffer from this affliction. Although medicines have been created that significantly diminish the suffering of migraine patients, these medicines are often contraindicated and have highly undesirable side effects and many patients do not obtain satisfactory relief from the severe headache pain, nausea and other discomforts associated with migraine. Furthermore, migraine headaches are typically treated after they have become painful, i.e. the treatment is often ineffective in preventing the onset of the migraine headache. Other than some drugs that are efficacious for some patients, there is currently no known treatment for migraine headaches that can be applied after a patient detects an aura of that headache to prevent the occurrence of pain and other undesirable manifestations of that migraine headache. A non-invasive, non-drug method for preventing the occurrence of migraine headaches would be a remarkable boon for those millions of people all over the world who suffer from these painful and often debilitating experiences.

In 1985, A. T. Barker, et al (Lancet, 1985, pp. 1105-1107) described the use of a coil placed over the scalp which produced a high intensity, time varying, magnetic field. This magnetic field produces an electric current in the cortex of the human brain which can in turn produce certain effects on brain neurons. This type of system has been given the name Transcranial Magnetic Stimulation (TMS). If continuously repetitive magnetic pulses are applied in this manner, it has been given the name rTMS.

In an article from Advances in Therapy, May/June 2001 and entitled "Impulse Magnetic-Field Therapy for Migraine and Other Headaches: A Double-Blind, Placebo-Controlled Study," by R. B. Pelka, et al, there is described a device using an alternating magnetic field source placed on a ribbon around the patient's neck. All devices were no more than 12 inches from the patient's head. The intensity of the 16 Hz magnetic field at the source was 5 microTesla. For all patients, the field at the brain had to be less than 1.0 microTesla. This field was applied for 4 weeks with some benefit being reported in 1 to 3 weeks. The wearing of such a device for weeks is certainly inconvenient as compared to a single magnetic pulse applied for a fraction of a millisecond or at most, a few such pulses. It is also believed that a magnetic field strength of only 1 microTesla would be totally insufficient to erase the aura that precedes many migraine headaches.

In the journal Neurology (Apr. 11, 2000, pp. 1529-1531) it has been reported by B. Boroojerdi, et al that rTMS at a rate of one pulse per second can create a reduction of the excitability of the neurons of the human visual cortex. However, that article did not indicate that TMS or rTMS can be used for the preventing the occurrence of migraine headaches or diminishing the intensity or duration of a migraine headache.

In U.S. Pat. No. 6,402,678, Robert E. Fischell et al describe means and methods for the treatment of migraine headaches using a portable device that is placed onto the patient's head. This device is used to create a magnetic pulse that acts upon the neurons of the brain and can eliminate both the aura that occurs prior to a migraine headache and a migraine headache after it has started. However, since the entire device is placed onto the patient's head, it is somewhat awkward for the patient's use. Furthermore, since the triggering controls are also located on the head mounted device, their operation is also somewhat difficult.

In U.S. patent application Ser. No. 10/929,586, Robert E. Fischell et al describe an improved device for applying TMS to the neurons of the brain. However, that application does not describe any means to limit the number of TMS pulses that a patient can place onto his or her head, nor does that application describe any means for verifying that the TMS device is operating properly. Still further, that prior application did not conceive of the main features of the present invention which is a one-piece, hand-held portable unit that contains all the circuitry and a magnetic coil for applying a TMS pulse onto the patient's brain.

SUMMARY OF THE INVENTION

The present invention is a means and method for improving the treatment of any number of disorders of the brain that can be treated by creating electric currents in the brain by the application of a high intensity, short duration magnetic pulse or a series of such pulses. An example of such diseases includes all types of headaches, depression, obsessive-compulsive disorder, insomnia, bipolar disease, epileptic or febrile seizures and status epilepticus. It is also anticipated that an intense, short duration, magnetic pulse or a collection of pulses could be applied as therapy by stimulation of a variety of nerves such as the occipital nerve or the trigeminal nerve in the region of the head and the vagal nerve in the region of the neck. It is also anticipated that magnetic pulses applied to the carotid sinus and/or vagal nerve in the neck can be used to stop an episode of atrial fibrillation.

For the purposes of this disclosure, the use of a single TMS pulse or several TMS pulses for the treatment of migraine headache will be described in detail. However, it should be understood that the system used for the treatment of migraine headache could also be used for the treatment of other disorders such as those mentioned herein. It should be understood that multiple magnetic pulses could be used instead of a single pulse. These multiple pulses could either be a multiplicity of single pulses that are spaced apart by a few seconds to several minutes, or they could be rTMS which is a continuous train of magnetic pulses. Although the patient will be described in this specification as being of the female gender, it should be understood that the invention can be used by either males or females and by children or adults.

The present invention is a single unit, portable magnetic pulser that can be placed by the patient onto any region which is in contact with or is placed near her head. The pulser can be powered by a battery, from a wall receptacle or from an automobile's lighter receptacle. After the pulser is plugged into a power source, a charge switch can be pressed by the patient to begin charging the capacitors to a comparatively high voltage.

When this occurs, a visual display would clearly indicate that the capacitors are charging. Ideally, a line of LEDs would turn on from one end to the other indicating the progression of the charging cycle. Alternatively, it is conceived that the TMS pulser could employ a linear bar that progressively fills with light as the capacitors are charged. When the capacitors are fully charged, a visual indicator, such as a lit green LED, would show that the capacitors are now ready to be discharged into a low resistance coil to produce a high intensity, short duration, magnetic pulse. It is highly desirable that the visual display used would be of a color and intensity (e.g., a dim blue light) that would be minimally disturbing to any person having a migraine headache. Examples of such visual displays include a series of LEDs or an LCD display (monochrome or color).

To increase battery life and/or prevent accidental charging of the capacitors, the charge switch could be under a cover, be a slide or rotary switch, require activation for a fixed period of time or any other technique that provides a means to prevent inadvertent charging. If the charge switch is accidentally pressed, disconnecting the source of electric power will prevent the capacitors from becoming fully charged.

Before the patient presses the button to discharge the capacitors into the magnetic coil, she would have placed the bottom surface of the pulser against her head or any other region of her body where the magnetic pulse would be therapeutic. The high intensity, short duration, magnetic pulse would, by Faraday's Law, create electric currents in the neurons of the brain (or elsewhere in the body) that would be a treatment for the patient's disorder. For example, if the magnetic pulse was applied to the occipital lobe of the brain during the visual aura before a migraine headache, the aura could be substantially erased and the patient would not progress to having a migraine headache. The magnetic pulse applied to another region of the body could be used to generate an electric current pulse at that location, which electric current pulse could be therapeutic.

An important factor in the design of the TMS pulser is its ability to limit the number of pulses that the patient could apply to her brain without authorization from the physician who prescribed the device for the patient's use. If there were an unlimited number of pulses that the device could deliver, a patient might allow an unauthorized person to use the device without a proper prescription from a doctor. By limiting the number of pulses that could be applied without a refill prescription from the patient's doctor and by charging a moderate amount of money for each pulse that is used, the patient will not be tempted to allow others to use her pulser. It should however be understood that a device which can apply an unrestricted number of pulses is conceived of as included in the concept of the present invention.

A potential safety aspect of this invention is that the TMS pulser could limit the number of pulses per unit time that the patient could receive. For example, the device could be designed to disallow more than (let us say) ten pulses in any one hour period.

To satisfy the need for a refill of available pulses, the pulser could include a standard RJ-11 telephone jack that the patient could use to allow the device manufacturer to add pulses over a telephone connection as allowed by a refill prescription from the patient's doctor. Also, the telephone connection could be used to transmit date and time stamped pulse usage from the TMS pulser to the patient's doctor or a central diagnostic center for patient monitoring. The telephone connection could also provide device diagnostics if the pulser was not operating properly. An alternative means for providing additional pulses and reading data into and out of the pulser would be by means of a USB key or any other device that would connect to a standard type of computer input connection such as an Ethernet connection. When inserted into the pulser, the USB key could be used to increase the number of allowed pulses. Of course, any refill of pulses would have to be authorized by a valid and current refill prescription from the patient's doctor.

The USB key would typically be a standard USB thumb drive with encoded data that will instruct the TMS pulser to allow a prescribed number of allowed pulses. In any case, the TMS pulser would be designed so that the USB key would only enable additional pulses once as removing and reinserting the USB key a second time would have not add additional pulses.

It is envisioned that other telecommunications interfaces such as Wi-Fi or wired Ethernet through the Internet could be used instead of a telephone connection. In addition, other standard flash memory devices such as a compact flash card, memory stick or SD card could be used instead of the USB thumb drive or USB key.

Because (using one mode of the present invention) there would be a limited number of pulses available to the patient, it would be important for the patient to know the exact number of pulses remaining. To that end, an LCD, LED (or other) display (or audio) could be provided that indicates the number of pulses remaining. If the number of available pulses dropped to that number that would be used by the patient in only a few days, the patient could ask the doctor for a refill prescription or the refill prescription could be on file with the organization that provides a variety of patient services. The patient could then receive a refill from the patient services organization through the telephone connection or by means of the USB key. It should be understood that once a patient has a previously used USB key, a refill could be accomplished by the use of the USB slot in a personal computer that is connected over the Internet to the TMS pulser manufacturer (or an authorized service organization) who could verify the refill prescription and the source for payment for the pulses and send the properly encoded data to the USB key to permit additional pulses. The patient would then remove the updated USB Key and insert it into the TMS pulser.

It is also understood that the USB key could be sent by mail or purchased at the patient's local pharmacy. It should also be understood that a date and time stamped history of the number of pulses used could be made available to the doctor or the manufacturer by means of the telephone connection or the USB port from data stored in a digital memory in the pulser. The USB port would work by either connecting using a cable to a PC or by transferring the data to the USB key which is then inserted in a the USB slot of a computer connected to the Internet.

It should be further understood that the magnetic pulser system could include a self-checking means that would verify that the magnetic pulse was within a specified limit of amplitude and time duration. This could be accomplished by a separate wire coil located near the device's magnetic coil that would measure the amplitude and time course of the magnetic pulse. If either the amplitude or time course of the magnetic pulse were out of their specified limits, the magnetic pulser system could produce an error signal that would be detected by the patient and could also be determined by a patient's service center via a telephone or Internet connection. The warning could be by means of a visual display or by means of a voice warning. Additionally, the patient could be provided with a separate device that could be used to check the amplitude and time course of the magnetic pulse. This could be an external device onto which the patient places the TMS pulser, then actuates the pulser and then the external device measures the magnetic pulse. It is also envisioned that a closed-loop control system could be used where the level measured on the previous pulse could be used to change the charge parameters on subsequent pulses to maintain the magnetic pulse within pre-defined limits. Such calibration could be manual (there is a calibrate button) or automatically done each time the TMS pulser pulses.

Another important aspect of the invention is that each pulser would have a unique serial number that is recorded for a particular patient. When the TMS pulser transmits the stored data on pulse usage or receives instructions to add pulses, the data transmitted to and from the TMS pulser must be encrypted so that it would be essentially impossible for an unauthorized person to add pulses to the pulser or to gain access to the patient's use of pulses to treat her brain (or other) disorder. Furthermore, a secure link could allow the patient to be recognized only by her serial number so that her actual name would not be known to the operator at the manufacturer's service center. Thus patient confidentiality would be maintained.

Another important aspect of the present invention is the shape of the magnetic coil. In U.S. Pat. No. 5,116,304, J. A. Cadwell describes a magnetic coil that has the shape of a skull cap. Although this design can function to provide a TMS pulse, the present invention describes an improved coil design which can be in the form of a racetrack, a true ellipse or a quasi-elliptically shaped coil. Any of these shapes of a coil that is generally longer in one direction compared to the length at a right angle to the coil's long axis will be described herein as being elliptical in shape. The elliptical coil would be curved around its short axis to generally suit the curvature of a human head. The curved, elliptical shape for a TMS magnetic coil allows both the left and right occipital lobes to be stimulated at the same time. Thus, to erase the visual aura of a migraine headache, the patient would merely have to center the long axis of the coil over the centerline of occipital lobe of the head and she would then erase the aura irrespective of which side of the occipital lobe was the source of that visual aura.

Although TMS systems that have been used for many years for brain research purposes are capable of creating a magnetic pulse that could usefully be used for therapeutic purposes, all prior TMS systems have been very large and weigh over 50 pounds. Therefore, they are not really portable for a typical patient. Furthermore, these systems are never operated by the patient but rather they are operated by the medical personnel who are performing the brain research experiment. One preferred embodiment of the present invention is for a truly portable device that could be carried in at least a large pocketbook of a woman patient. The present invention therefore defines a portable magnetic pulser system to be a TMS device that is operated by the patient and weighs less than 10 pounds. Optimally the pulser weighs less than 4 pounds. However, it should be understood that the present invention could be a non-portable magnetic pulser system that weighs more than 10 pounds and remains most of the time in the patient's home (or another site where the patient spends most of her time) for use as needed. However, in all cases, the TMS magnetic pulser would be operated by the patient.

Thus one object of the present invention is to have a magnetic pulser that is portable and operated by the patient for the treatment of disorders of the brain or other human organs, the magnetic pulser being designed to provide one or more, high intensity, short duration, magnetic pulse that is applied to the neurons of the brain or to any other body part that is to be treated.

Another object of this invention is to limit the total number of pulses available before a refill takes place and also to limit the number of pulses allowed in a predefined time period.

Still another object of this invention is to have the availability of additional magnetic pulses provided by means of a telephone (or Internet) connection or from a USB key from an authorized provider of the pulses and based upon a refill prescription from the patient's doctor.

Still another object of this invention is to have the refill data message in an encrypted format so that a refill of pulses cannot be accomplished without proper authorization.

Still another object of this invention is to have a curved, elliptically-shaped coil for the pulser that can create a magnetic pulse over either or both sides of the occipital lobe of the brain.

Yet another object of this invention is to have a visual display on a TMS pulser that can show the number of pulses remaining, the status of the charging cycle and that the capacitors are fully charged.

Yet another object of this invention is to have a means to prevent inadvertent activation of the charge switch which starts the capacitor charging cycle.

Yet another object of this invention is to have the visual displays be designed to minimize discomfort for a person experiencing a migraine headache.

These and other objects and advantages of this invention will become obvious to a person of ordinary skill in this art upon reading the detailed description of this invention including the associated drawings as presented herein.

DETAILED DESCRIPTION OF THE INVENTION

Figures 1, 2:
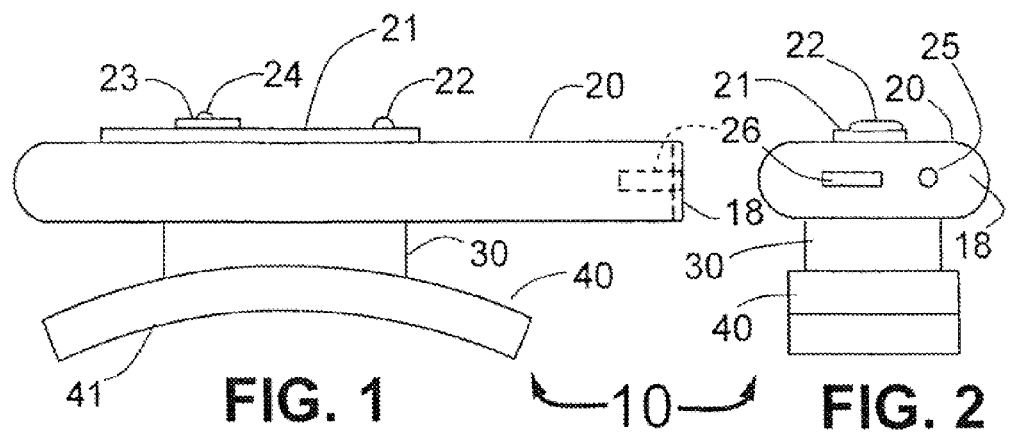
FIG. 1 is a side view of the magnetic pulser system for the treatment of disorders of the brain or other body tissue or organs.
FIG. 2 is an end view of the magnetic pulser system showing the receptacles for both a power cord and a USB key.
Figure 3:
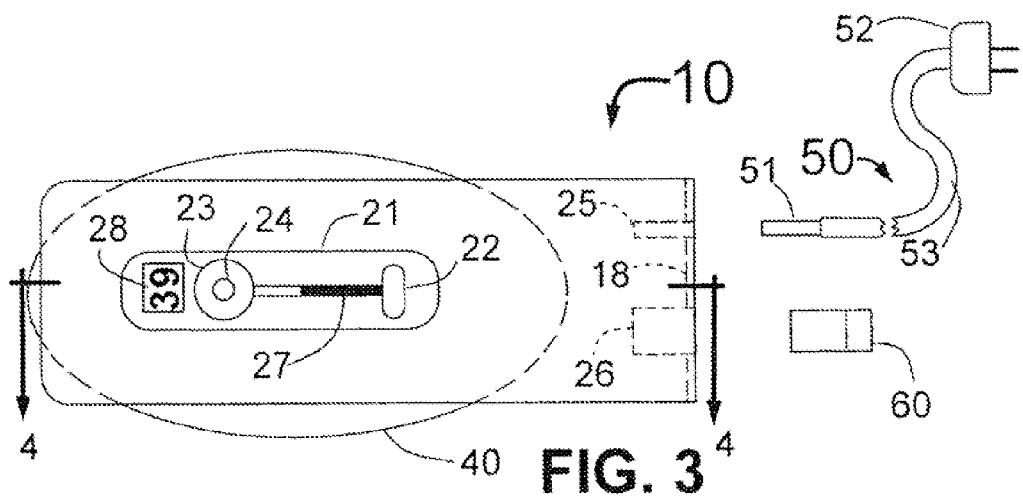
FIG. 3 is a top view of the magnetic pulser system showing the information and control display panel and also a power cord to power the magnetic pulser system.
Figure 6:
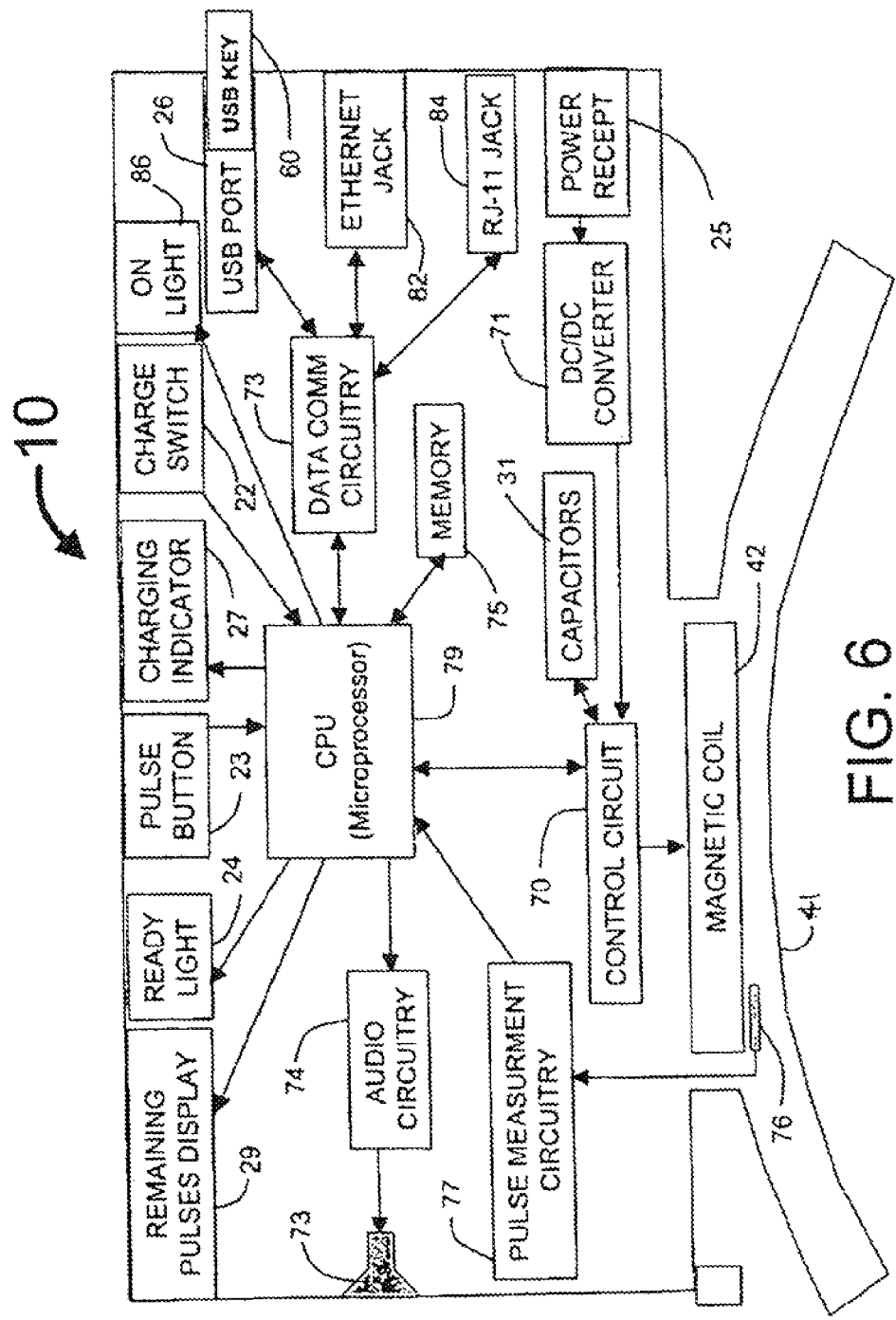
FIG. 6 is a block diagram of the electronics of the magnetic pulser system.

FIGS. 1, 2 and 3 are respectively the side view, end view and top view of the magnetic pulser 10. These FIGS. 1, 2 and 3 show the electronics section 20 joined to the magnetic coil section 40 by the connecting structure 30. FIGS. 1, 2 and 3 show the information and control display panel 21 that includes a charge switch 22, a pulse button 23, a ready light 24, a charging indicator bar 27 and a number of pulses remaining display 28. FIG. 3 shows that the number of pulses remaining is 39. When the plug 51 of the power cord 50 (of FIG. 3) is plugged into the power receptacle 25, the number of pulses remaining display is illuminated. This immediately tells the patient that the magnetic pulser 10 is powered. If the magnetic pulser 10 has self-contained batteries, or for any other reason, an ON-OFF switch (not shown) would or could be utilized. When the magnetic pulser 10 is powered, the patient can press the charge switch 22 which causes the capacitors 31 (as seen in FIGS. 4 and 6) to begin to charge.

The extent to which the capacitors 31 are charged is shown by the charging indicator bar 27. Instead of a charging bar, a sequence of individual lights could also be used to indicate that the capacitors 31 are being charged. WMaen the capacitors 31 are fully charged, the bar 27 is fully illuminated and the ready light 24 turns on. When that occurs, the patient can place the curved surface 41 of the magnetic coil section 40 against her head and then press the pulse button 23 which will discharge the capacitors 31 into the magnetic coil 42 (shown in FIGS. 5 and 6). This creates the TMS magnetic pulse that can depolarize the neurons of the brain therefore erasing a visual aura and preventing the occurrence of a migraine headache. Whenever a pulse is created, the number of pulses remaining display 28 decreases by one. To prevent accidental charging of the capacitors 31, the charge switch 22 could be under a cover, be a slide or rotary switch, require activation for a fixed period of time or any other technique that provides a means to prevent inadvertent charging.

FIG. 3 shows one form of a power cord 50, namely the type that would be plugged into a typical household receptacle. This power cord 50 has a plug 51 that is electrically connected to a transformer-rectifier 52 by means of wires 53. The transformer-rectifier 52 would have two or three prongs to be plugged into the household receptacle that is typically 115 volts AC in the USA. It is also conceived that a different type of power cord could be plugged into a conventional cigarette lighter (or other power source) in an automobile. In any case, it would be typical that the voltage at the plug 51 would be 12 volts DC. It is also anticipated that a power cord could be joined to a battery that had either primary cells or rechargeable cells either of which could be used to power the magnetic pulser 10. It is further understood that the magnetic pulser 10 could have a self-contained battery that was either rechargeable or used replaceable cells. FIGS. 1, 2 and 3 also show a receptacle access wall 18 into which the power receptacle 25 and a USB key receptacle 26 could be placed. The USB key receptacle 26 would be used with a USB key 60 of FIG. 3 as will be explained below with the assistance of FIG. 6.

Figure 4:
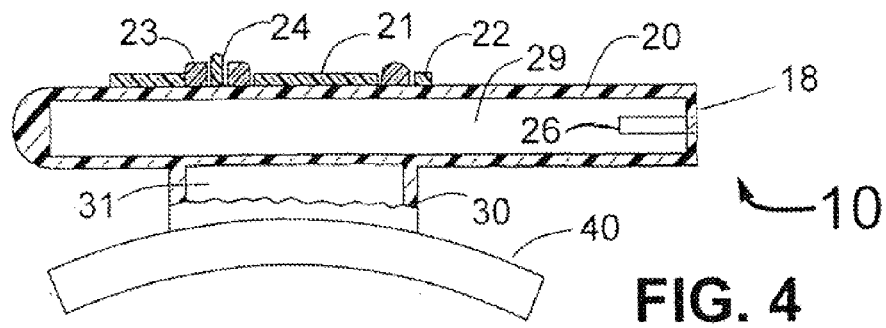
FIG. 4 is a partial crossectional view of the magnetic pulser system.

FIG. 4 is a partial cross section of the magnetic pulser 10 showing a cross section of the display panel 21 that includes the charge switch 22, the pulse button 23 and the ready light 24. FIG. 4 also shows the receptacle access wall 18, the connecting structure 30 and the magnetic coil section 40. One or more capacitors 31 are shown within the connecting section 30. The electronics module 29 is shown within the electronics section 20. The components within the electronics module 29 will be described below with the assistance of FIG. 6.

Figure 5:
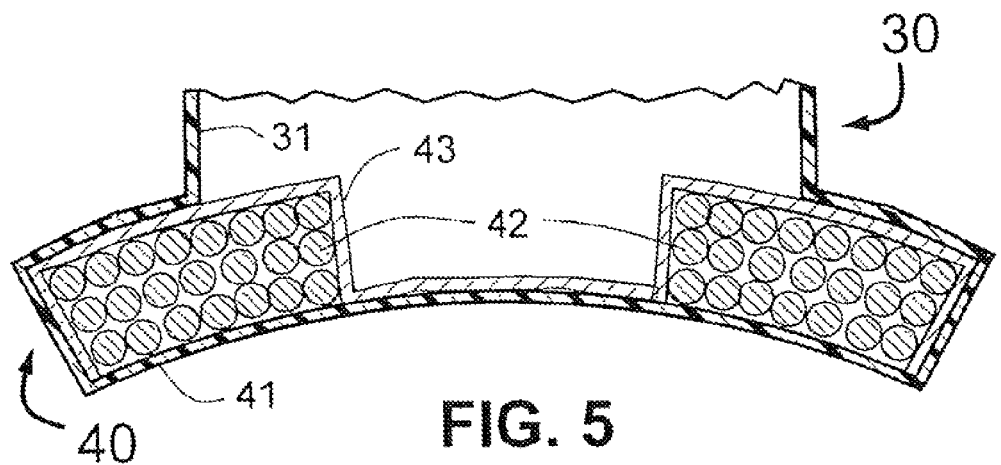
FIG. 5 is a cross section of the pulser showing the arrangement of the magnetic coil.

FIG. 5 is a cross section of the magnetic pulser 10 showing the connecting structure 30 as it is joined to the magnetic coil section 40. The plastic molded wall 31 is formed generally around the entire magnetic pulser 10. The curved surface 41 of the magnetic coil section 40 is designed to be approximately the same curvature as a human head. An exact match to the curvature of any particular head is not required for the therapeutic effect to be achieved. A curvature for the surface 41 having a radius that is greater than 3 inches and less than 6 inches would be acceptable for the magnetic pulser system 10. A radius of curvature of approximately 4.5 inches would be satisfactory for most patients. It is conceived that the exact curvature for any patient could be approximately matched to the curvature of her specific head. For example, it is conceived that the manufacturer could make three different curvatures for heads having either a small, medium or above average curvature.

FIG. 5 also shows the general arrangement of the electrical wire that forms the magnetic coil 42. Although FIG. 5 shows the electrical wire to be solid metal (which could have an insulating covering) with a conventional circular cross section, an improved design would be Litz wire that includes many strands that are each insulated from the other strands of the wire. Another good cross section for the wire would be rectangular with a very thin dimension (0.001 to 0.1 inches) in one direction and a dimension between 0.2 and 0.8 inches in the orthogonal dimension. An optimum design would be Litz wire having a square cross section of the collected strands. Although copper would be an adequate metal from which the magnetic coil 42 could be made, pure aluminum wire would have the advantage of being considerably lighter. The optimum wire for the magnetic coil 42 would probably be aluminum Litz wire that has a square or rectangular cross section.

FIG. 5 also shows a single magnetic lamination 43 which is formed to the shape of the magnetic coil 42. Although only one lamination is shown, it is conceived that a multiplicity of magnetic laminations could be used to increase the magnetic field strength in the direction of the head while decreasing the magnetic field intensity in the direction of the connecting structure 30. The ferromagnetic material from which the lamination(s) 43 could be made include silicon iron or any other magnetic material that has a comparatively high permeability and saturation flux density.

FIG. 6 is a block diagram of the magnetic pulser system 10. The power receptacle 25 (from an outside power source) energizes a DC to DC converter 71 (or an AC to DC inverter that is not shown) to provide the appropriate power for all of the electronics shown in FIG. 6. The output of the converter 71 goes to the control circuit 70 which controls the charging and discharging of the capacitors 31. A high voltage line (typically between 300 and 800 volts) is used to charge the capacitors 31. Although a single high voltage capacitor might be used, a combination of at least two capacitors in series or in parallel is often more advantageous.

The magnetic pulser system 10 is controlled by the central processing unit (CPU 79) which follows the instructions stored in the memory 75. When power is applied to the power receptacle, the CPU 70 will boot-up from the memory 75 and the power on light 86 will light. Instead of a power on light, the number on the remaining pulses 29 could illuminate to indicate that the power is on. The CPU 79 will also enable the appropriate number to be shown on the remaining pulses display 29. The memory 75 should include at least a portion of non-volatile memory so that the remaining number of pulses and patient data will be retained when the system 10 is unplugged from a power source or turned off.

Once the CPU 79 has been booted up, the system 10 is ready to be used. Assuming there are remaining pulses, the patient would activate the charge switch 22 which would cause the CPU 79 to activate the control circuit 70 to begin charging the capacitors 31. As the capacitors 31 are charging, the control circuit 70 monitors the voltage and communicates this information to the CPU 79 which activates the charging indicator bar 27 which is typically a continuously illuminated bar, or alternatively, a linear array of LEDs where first one LED is lit, then two, then three and so on until the entire array is lit as the capacitors 31 reach their full charge. When the capacitors 31 are fully charged, the CPU 79 will activate the ready light 24 which is typically green. The patient would then place the surface 41 of FIG. 5 against the appropriate part of the head (or other body part) and then depress the pulse button 23 which will signal the CPU 79 to instruct the control circuit 70 to discharge the capacitors through the magnetic coil 42. A preferred embodiment of the pulse button 23 integrates the ready light 24 into the button 23.

When the magnetic pulse is triggered, the ready light 24 goes off, the illuminated bar on the charging indicator bar 27 turns off and the remaining pulse display 29 will show one less pulse.

An additional feature of the electrical circuitry of the magnetic pulser system 10 is that when the ready light comes on, the audio circuitry 74 could provide an audio signal (that is a verbal signal) through the speaker 73 which indicates to the patient that the magnetic pulser system 10 is ready to provide a magnetic pulse. When the pulse is completed, the audio circuitry 74 through the speaker 73 could also state that the pulse has been delivered. Additional audio signals could provide other messages such as there is an error and the device is not functioning or the voltage is too low, or there are only a limited number of pulses remaining, etc. In whatever country the device is sold, the audio signal could be in the language of that country or even in the language or dialect of a limited region of a country.

A USB key 60 when inserted in to the USB port 26 could be used to increase the number of pulses remaining by a specific number as specified in the doctor's refill prescription and as paid for by the patient. For example, a refill accomplished by the USB key could be for 25, 50 or 100 additional pulses. The CPU 79 and memory 75 could also hold an encrypted security code that disallows any input for additional pulses that is not provided by the manufacturer's service center. Furthermore, the memory 75 could store the date and time for each pulse that is delivered by the TMS pulser system 10. The time history of the patient's use of pulses can be stored in the memory 75 and could be read out through the data communication circuitry 73 through the USB port 26, the Ethernet jack 82 or the RJ-11 telephone jack 84.

To monitor the shape of magnetic pulses delivered by the magnetic pulse system 10, a small magnetic field detection coil 76 would be placed in close proximity to the magnetic coil 42. The coil 76 would feed into the pulse measurement circuitry 77 that would tell the CPU 79 to illuminate an error signal light (not shown) on the magnetic pulser system 10 if the amplitude and/or duration of the magnetic pulse was out of a pre-specified range. The letters "E" or "ER" could also appear on the pulse counter to indicate that an incorrect pulse was generated. The patient may also be warned that the pulse was out of its specified limits by means of the audio circuitry 74 and the speaker 73. By means of the USB port 26 or a data communications connection through the Ethernet jack 82 or R J-11 telephone jack 84, a technician at the patient's service center could determine if the magnetic pulse was within its specification and also the exact time history of each magnetic pulse. Thus each device in the patient's hands could be checked to see that it was performing properly. To avoid tampering, it is envisioned that the opening of the case would result in the magnetic pulse system 10 becoming completely inoperative. This could be through erasure of the boot instructions in the memory 71 or through other means.

Figure 7:
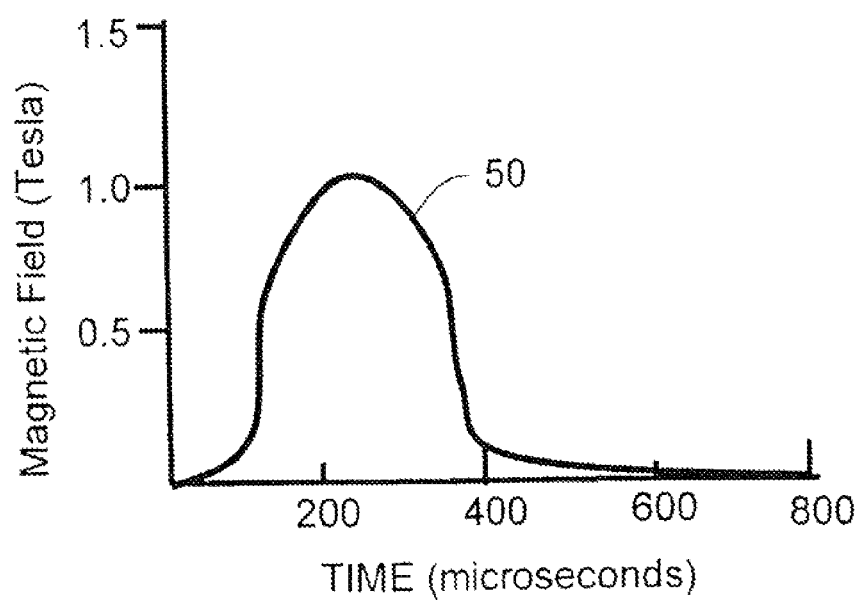
FIG. 7 illustrates the time course of the magnetic pulse.

FIG. 7 shows a typical magnetic pulse that can be created when the capacitors 31 are discharged into the magnetic coil 42. Ideally, the peak magnetic field of about 1.0.+−.0.5 Tesla would be created at the center of the bottom surface of the magnetic coil 42. The time to reach the pulse's maximum field strength should ideally be 175.+−.100 microseconds, although the time to maximum pulse strength could vary from as little as 10 microseconds to as long as 10,000 microseconds. What is most important is that the time rate of change of the magnetic pulse be fast enough to create a therapeutic electric current in the brain or other human tissue. The maximum value of the strength of the magnetic field within the brain should be at least 0.05 Tesla. If the maximum value of the field within the brain is less than 0.05 Tesla, the magnetic pulser system 10 will not function for many patients. To create a magnetic field in the brain that is greater than 5 Tesla, would require an excessive weight and size of the magnetic pulser system 10. Thus, the acceptable range for the maximum value of the magnetic field within the patient's brain should lie between 0.05 and 5.0 Tesla. The optimum range for the maximum magnetic field strength onto some part of the patient's brain should lie between 0.2 and 1.0 Tesla.

It should be understood that an effective magnetic pulser system 10 could be created that utilizes some but not all of the features as described herein. For example, a magnetic pulser system could be created and work effectively without a pulse counting feature. Another example are the audio signals for the patient which could also be eliminated and still an effective magnetic pulser system could function for the treatment of migraine headache and other disorders. These are just two examples of the several that could be eliminated and the magnetic pulser system 10 would still be of value for most patients. It should also be understood that the use of the word "capacitors" has the meaning of one or more capacitors.

Various other modifications, adaptations and alternative designs are of course possible in light of the teachings as presented herein. Therefore it should be understood that, while still remaining within the scope and meaning of the appended claims, this invention could be practiced in a manner other than that which is specifically described herein.

What is claimed is:

1. A portable magnetic pulser system for the treatment of migraine headaches of a human subject who is a migraine headache patient, the system including:
   an electrical power source for operating the system;
   electronic circuitry located within an enclosure for taking power from the electrical power source for charging at least one capacitor;
   control circuitry located within said enclosure that is capable of charging the at least one capacitor and then dumping the charge into a magnetic coil that is used to create an intense magnetic pulse onto the brain of the human subject, the charging of the capacitors and the discharge of the capacitors into the magnetic coil being individually controllable by at least one electrical switch that is operated by the patient, the maximum intensity of the magnetic pulse delivered onto the brain of the human subject being between 0.05 and 5.0 Tesla;
   a processor mounted within said enclosure, said processor coupled to the electronic circuitry and the control circuitry, the processor configured to:
   (1) limit the total number of magnetic pulse treatment sessions that the patient can apply to himself or herself over a period of time before a prescription expires;
   (2) calculate a remaining number of pulse treatment sessions which may be applied before a prescription expires; and
   (3) disable said magnetic pulser system when said enclosure is at least partially opened; and
   a means to indicate the number of pulses remaining for the patient's use in a selective time interval.

2. The magnetic pulser system of claim 1 where there is an audio signal indicating that the magnetic pulser system is not operating properly.

3. The magnetic pulser system of claim 1 including means for refilling the number of pulses remaining for the patient's use based upon a prescription from the human subject's doctor.

4. The magnetic pulser system of claim 3 where the means for refilling is accomplished over a telephone line from a manufacturer's service center.

5. The magnetic pulser system of claim 3 where the means for refilling is accomplished using a USB key.

6. The magnetic pulser system of claim 5 where the USB key can have the number of pulses to be added made available through the USB port of a computer that is in contact over the Internet with a manufacturer's service center.

7. The magnetic pulser system of claim 1 also including means for date and time stamping of each magnetic pulse that is triggered, the data being stored in a digital memory of the magnetic pulser system.

8. A method for the treatment of a disorder of a human patient, the method including the following steps:
   a) procuring a magnetic pulser system that is capable of delivering a magnetic pulse having a maximum magnetic field intensity that lies between 0.05 and 5.0 Tesla;
   b) sensing by the patient when an illness occurs;
   c) having the patient initiate the charging of at least one capacitor in the magnetic pulser system to a high enough voltage to generate the desired magnetic pulse upon an affirmative determination by the magnetic pulser system that the prescribed number of treatment sessions has not been exceeded;
   d) placing by the patient of a magnetic coil onto a region in close proximity to a specific problematic nerve of the human body, these specific nerves including at least one nerve selected from: the occipital nerve, carotid sinus and the vagal nerve in the neck; and
   e) triggering by the patient of the capacitors to directly discharge into the magnetic coil to provide the desired magnetic pulse to the specific problematic nerve;
   wherein a processor mounted within an enclosure is configured to disable said magnetic pulser system when said enclosure is at least partially opened.

9. A portable magnetic pulser system for the treatment of migraine headaches of a human subject who is a migraine patient, the system including:

an electrical power source for operating the system;

electronic circuitry located within an enclosure for taking power from the electrical power source for charging at least one capacitor;

control circuitry located within said enclosure that is capable of charging the at least one capacitor and then dumping the charge into a magnetic coil that is used to create an intense magnetic pulse onto the brain of the human subject, the charging of the capacitors and the discharge of the capacitors into the magnetic coil being individually controllable by at least one electrical switch that is operated by the patient, the maximum intensity of the magnetic pulse delivered onto the brain of the human subject being between 0.05 and 5.0 Tesla;

a processor mounted within said enclosure, said processor coupled to the electronic circuitry and the control circuitry, the processor configured to indicate to the patient that the at least one capacitor is charged so that it is ready to be discharged into the magnetic coil, and further configured to limit the total number of magnetic pulse treatment sessions that the patient can apply to himself or herself over a period of time before a prescription expires; and a means to indicate the number of pulses remaining for the patient's use in a selective time interval;

wherein said processor is configured to disable said magnetic pulser system when said enclosure is at least partially opened.

10. The magnetic pulser system of claim 9 where the processor indicates that the capacitor is ready to be discharged via a visual means.

11. The magnetic pulser system of claim 10 where the visual means is the filling of a bar that is steadily filled as the capacitor is being charged and is fully illuminated when the capacitor is ready to be discharged.

12. The magnetic pulser system of claim 9 where the processor indicates that the capacitor is ready to be discharged via an audio means.

13. The magnetic pulser system of claim 12 where the audio means is a voice indicating that the capacitor is ready to be discharged.

* * * * *